(12) United States Patent
Choung et al.

(10) Patent No.: US 7,331,076 B2
(45) Date of Patent: Feb. 19, 2008

(54) ELECTRIC TOOTH BRUSH WITH A LATITUDELY OSCILLATING BRUSH HEAD

(76) Inventors: Soo Hwan Choung, 1029 S. Elden Ave. Apt. #106, Los Angeles, CA (US) 90006; Jae Won Choung, 1029 S. Elden Ave. #106, Los Angeles, CA (US) 90006

( * ) Notice: Subject to any disclaimer, the term of this patent is extended or adjusted under 35 U.S.C. 154(b) by 366 days.

(21) Appl. No.: 11/100,007

(22) Filed: Apr. 7, 2005

(65) Prior Publication Data
US 2006/0225230 A1  Oct. 12, 2006

(51) Int. Cl.
*A46B 13/02* (2006.01)
*A61C 17/00* (2006.01)

(52) U.S. Cl. ......................... 15/22.4; 15/22.1

(58) Field of Classification Search ................. 15/22.1, 15/22.2, 22.4
See application file for complete search history.

(56) References Cited
U.S. PATENT DOCUMENTS

| | | | | |
|---|---|---|---|---|
| 3,379,906 A | * | 4/1968 | Spohr | 310/50 |
| 3,577,579 A | * | 5/1971 | Duve et al. | 15/22.1 |
| 3,588,936 A | * | 6/1971 | Duve | 15/22.1 |
| 4,710,995 A | * | 12/1987 | Joyashiki et al. | 15/22.1 |
| 5,448,792 A | * | 9/1995 | Wiedemann et al. | 15/22.1 |
| 6,581,233 B1 | * | 6/2003 | Cheng | 15/28 |

* cited by examiner

*Primary Examiner*—Laura C Guidotti
(74) *Attorney, Agent, or Firm*—Eugene Oak (57) ABSTRACT

An electric motor driven toothbrush is provided. The head of the toothbrush of the current application oscillates latitude to the body of the toothbrush. One end of a specially designed shaft, with an annular portion developed at that end, is connected to an electric motor via gears. A replaceable toothbrush head is attached to the other end. The circular portion at one end of the shaft is an annular plate that has at least two protrusions developed perpendicular to the circular plane. The two protrusions may be in a rectangular form or arc form developed along the perimeter of the circular portion developed on the shaft. A circular plate attached, with a predetermined angle, to a gear that vertically penetrates the annular portion enables a latitude oscillation movement of the brush head. With the toothbrush of the current application, a user can automatically scrub his/her teeth longitudinally along the length.

2 Claims, 8 Drawing Sheets

ELECTRIC TOOTH BRUSH WITH A LATITUDELY OSCILLATING BRUSH HEAD

FIELD OF THE INVENTION

The present invention relates to a toothbrush, and more particularly to a toothbrush driven by an electric motor causing a scrubbing motion along the length of teeth of a user.

BACKGROUND OF THE INVENTION

Most of people unconsciously scrub their teeth horizontally though they are advised by dentists to scrub their teeth vertically. Many electric toothbrushes are developed to compromise such undesirable behavior of many people. One of the most advanced electric toothbrushes utilizes an ultra sonic generator. However, this toothbrush is too expensive for the general public, and the side effects of extended exposure of teeth and gums to an ultra sonic wave have not yet been determined. Various ways of tooth brushing: a lateral brushing in which a toothbrush is moved laterally or horizontally, a vertical brushing in which a tooth brush is moved in the longitudinal direction of teeth and a rolling brushing in which a tooth brush is rotated in the vertical direction. Among the brushes developed up to now, brushes move in the longitudinal direction of the teeth are too bulky and expensive for the gears that are used to change the rotational movement of an electrical motor to an oscillatory motion that is perpendicular to shaft connected to the motor.

DESCRIPTION OF THE PRIOR ART

U.S. Pat. No. 5,448,792 to Wiedemann, et al. illustrates a tooth-brush is provided which has a brush shank adapted to be driven electrically by a drive and provided with a brush-head having bristles, which brush-head performs movement, for example, a loosening movement whose frequency is higher than 30 Hz and whose amplitude is between 0.1 mm and 5 mm, which brush-head performs an additional movement, for example, a wiping movement having a frequency of between 1 Hz and 5 Hz. The combination of a rapid loosening movement and a slow wiping movement ensures that the teeth are cleaned in a thorough but gentle manner.

The major drawback of this art is that the electric motor and the brush head is connected via many means that are not connected coaxially. Therefore, the oscillatory movement is unstable.

U.S. Pat. No. 4,710,995 to Joyashiki, et al. illustrates a motor driven toothbrush, having a scrubbing shaft supported on a standard secured to an end plate of a housing and movable in a direction of the axis of the scrubbing shaft, a rolling shaft coaxially fitted to the scrubbing shaft and movable around the axis of the rolling shaft, first drive means driven by an electric motor for driving said scrubbing shaft reciprocally in the axial direction, second drive means driven by the rotation of the electric motor for swinging said rolling shaft reciprocally around the axis of the rolling shaft, and adapter means having a toothbrush unit and being detachably mounted to the rolling shaft and/or the scrubbing shaft, whereby the operator of the toothbrush can select the scrubbing motion or rolling motion of the toothbrush as desired. This tooth brush has too many gears and parts to convert the rotational movement of the electric motor to an oscillatory movement.

U.S. Pat. No. 3,588,936 to Duve illustrates An electric cordless tooth brushing device having a power handle with a drive shaft extending from one end there of and a toothbrush attachment which is securable to the remote end of said shaft. The power handle includes a battery-powered motor, which by means of a motion converting mechanism drives the shaft so that the rotary power of the motor is translated to an orbital motion at the toothbrush attachment. An improved electric switch is provided to control the tenderization of the motor. This electric brush also has too much bulky levers and gears for converting the rotational movement to biaxial movements.

U.S. Pat. No. 3,379,906 to Spohr illustrates an electrical appliance and, more articularly, to a rechargeable battery operated electric toothbrush having a plurality of selectively different brush motions. The toothbrush comprises a power driven unit having electri C motor means with a motor armature selectively rotatable in either a forward or a reverse direction. A drive mechanism is included in the unit for converting rotation of the motor to either reciprocating or oscillating motion of an output shaft. The output shaft is intended to drive a toothbrush pre-movably connected thereto. The drive mechanism provides reciprocal movement of the output shaft in response to rotation of the motor armature in one direction and oscillatory movement of the output shaft in response to rotation of the motor armature in the opposite direction.

None of the prior art illustrate a simple and unique electric motor driven tooth brush with a latitude oscillating brush head of the current application as described in the following specifications.

SUMMARY OF THE INVENTION

An essential object of the current application is to provide a practical electric motor driven toothbrush that is affordable for everyone and is able to perform a latitude oscillating scrubbing motion of the brush head as desired. An electric motor driven toothbrush has a housing with two end plates formed on one end portion of the housing. An electric motor and rechargeable battery is accommodated in the housing. The electric motor shaft is projected outward of the housing through the first end plate that is close to the motor. One end of the first small cylindrical gear having two kinds of teeth, developed vertically and series on one gear body, is connected to the electric motor shaft and the other end is rotatably fixed to the second end plate that is located close to the toothbrush head. Those two end plates surrounded by the brush handle case forms a space for gears. Second small cylindrical gear with one kind of teeth meets the first gear perpendicularly. The second cylindrical gear penetrates an annular portion of a specially designed shaft. A cylindrical plate is fixed to the second gear at the center thereof with an angle in the range of 10 to 35 degree. Both ends of the second gear are connected to the inner wall of the brush handle. One end of the specially designed shaft is rotatably fixed to the first end plate apart from the center. The other end of the shaft is connected to a brush head. At least two protrusions are developed vertically along the perimeter of the annular portion of the shaft. As the motor turns, the second gear turns vertically to the direction of the motor shaft turns. As the circular disc turns with the second gear, the sloped edge presses one of the protrusions on either side of the perimeter of the annular plate. Then the shaft, connected to the annular plate, oscillates as the circular plate touch and press one of the protrusions.

BRIEF DESCRIPTION OF THE DRAWINGS

FIG. 3-*a* is an over view of the assembly of the gears for the toothbrush of the current application.

FIG. 3-*b* is a side view of the assembly of the gears for the toothbrush of the current application.

FIG. 3-*c* is a side view of the assembly of the gears for the toothbrush of the current application seen from the first end plate.

FIG. 6-*a* is a side view of the first embodiment of the annular portion 'B' of the specially designed shaft of the current application seen from the bottom of the toothbrush.

FIG. 6-*b* is a side view of the first embodiment of the annular portion 'B' of the specially designed shaft of the current application seen from the side of the toothbrush.

FIG. 6-*c* is an over view of the first embodiment of the annular portion 'B' of the specially designed shaft of the current application.

FIG. 7-*a* is a side view of the second embodiment of the annular portion 'B' of the specially designed shaft of the current application seen from the bottom of the toothbrush.

FIG. 7-*b* is a side view of the second embodiment of the annular portion 'B' of the specially designed shaft of the current application seen from the side of the toothbrush.

FIG. 7-*c* is an over view of the second embodiment of the annular portion 'B' of the specially designed shaft of the current application.

DETAILED DESCRIPTION OF THE PREFERRED EMBODIMENTS

Figure 1:
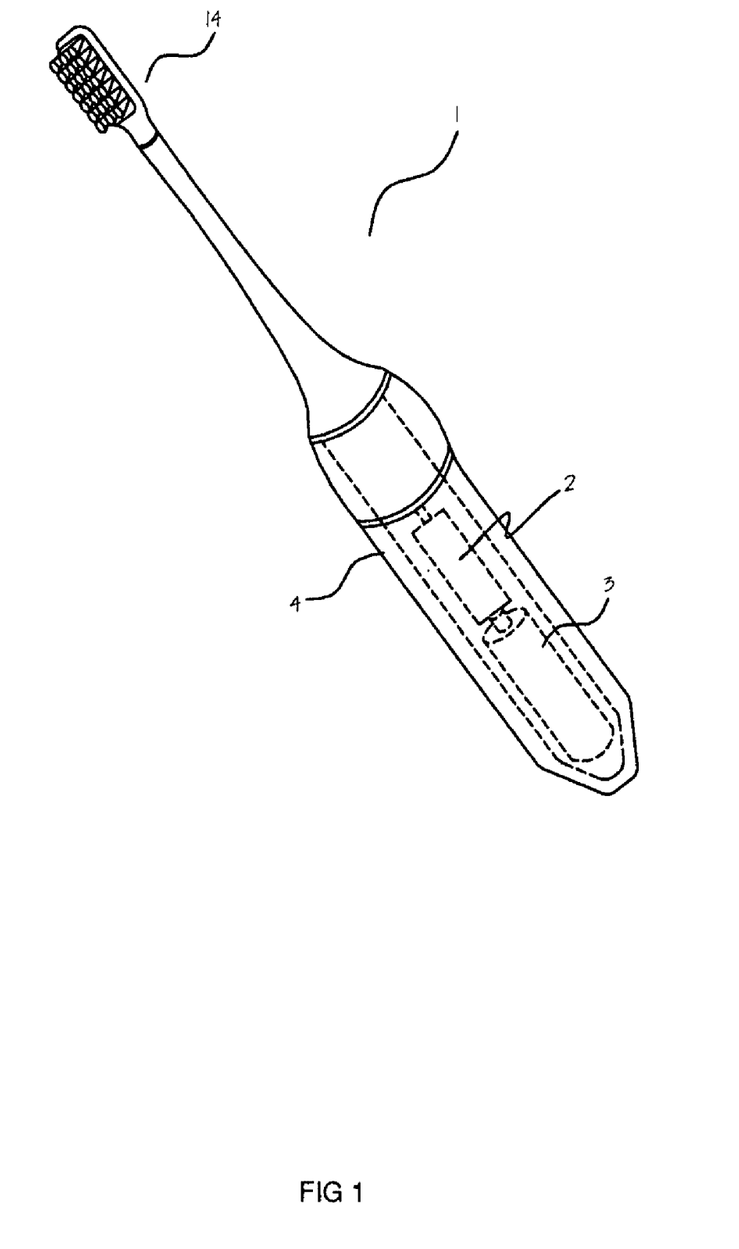
FIG. 1 is a perspective view of a toothbrush of the current application.
Figure 2:
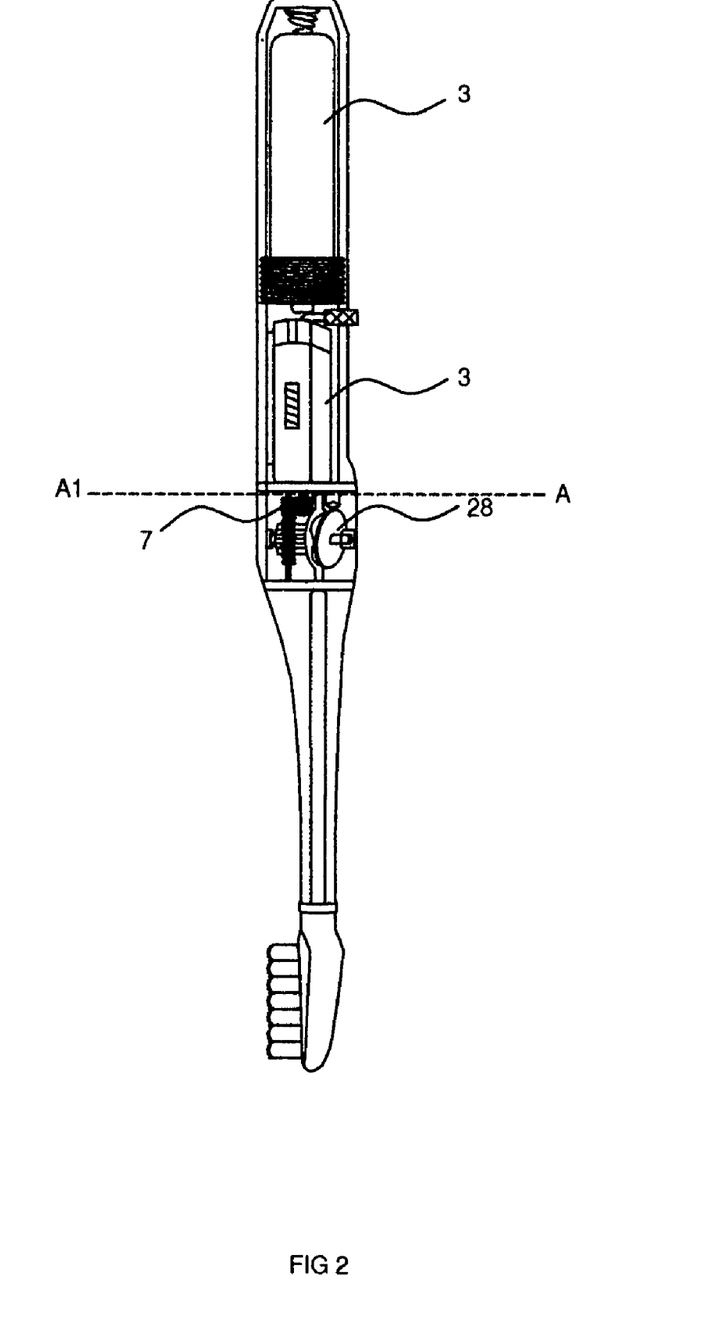
FIG. 2 is a side see through view of the toothbrush of the current application.
Figure 3A:
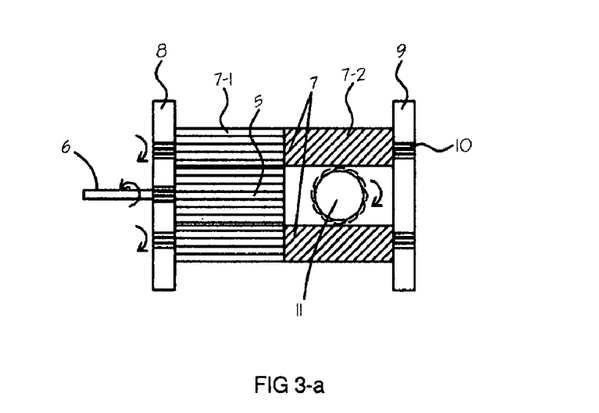
Figure 3B:
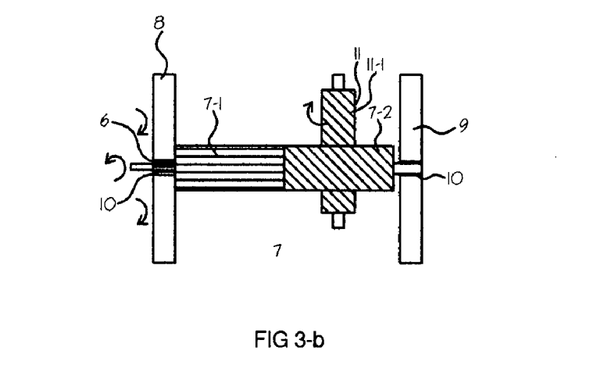
Figure 3C:
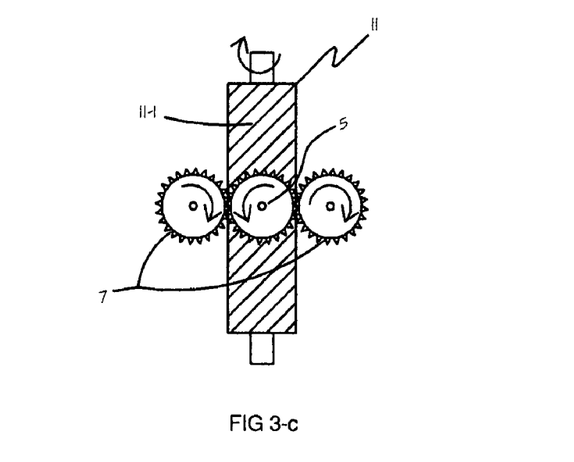

FIG. 1 is a perspective view of a toothbrush (1) of the current application. A small sized electric motor (2) and a rechargeable battery (3) are accommodated in a cylindrical chamber of a housing (4) of a handle portion of a toothbrush (1). FIG. 2 is a side see through view of the toothbrush (1). FIG. 3-*a* and FIG. 3-*b* are an over view and a side view of the assembly of the gears for the toothbrush of the current application, respectively. A motor gear (5) mounted to the rotation shaft (6) of the motor (2) is coupled to two scrubbing drive gears (7). Those gears have straight blades (7-1) and sloped blades (7-2) in one body. Those three gears are rotatably supported on the first end plate (8) and second end plate (9) of the housing (4) via bearing equipped ring connector (10). Another scrubbing gear (11) with only sloped blades (11-1) is perpendicularly coupled to the two scrubbing drive gears. FIG. 3-*c* is a side view of the assembly of the gears for the tooth-brush (1) of the current application seen from the first end plate (8) showing, the rotation of each gears. When the motor gear (5) turns in one direction, counter clock wise for example, the other two scrubbing gears (7) turns in opposite direction, clock wise. Then the sloped blades (7-2) on both of the scrubbing gears turn the perpendicularly coupled scrubbing gear (11). Coupling two scrubbing gears (7) to the motor gear (5) enhances the driving force to the perpendicularly coupled gear (11) and stabilizes the motion of the perpendicularly coupled gear (11).

Figure 4:
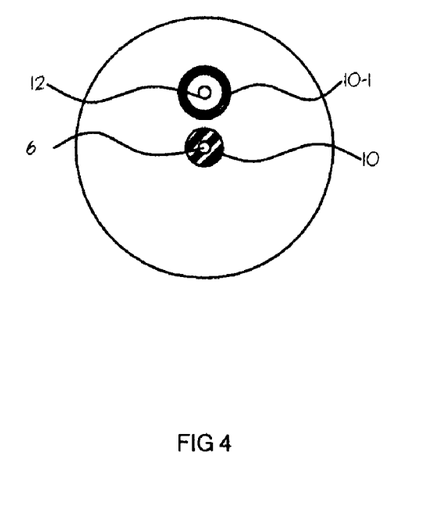
FIG. 4 is a cross sectional view seen from the bottom side of the tooth brush taken along the line A-A in FIG. 2.
Figure 5:
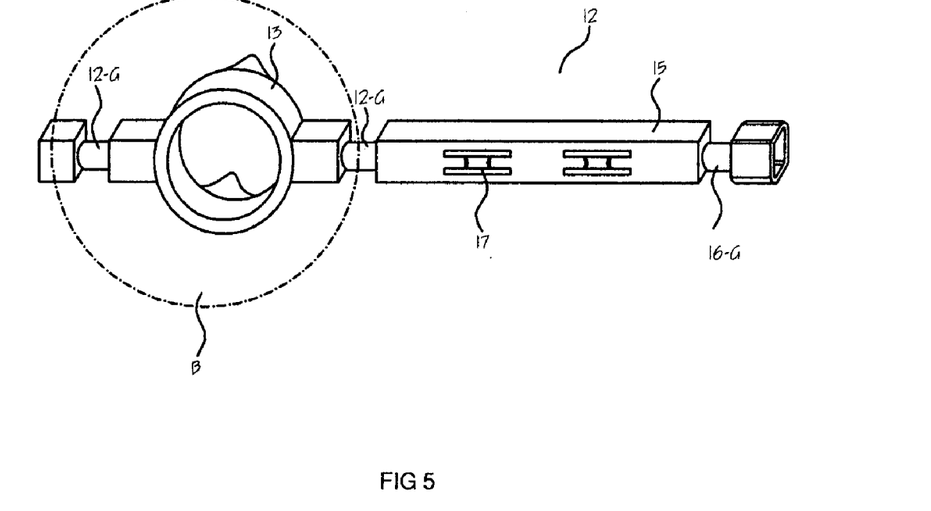
FIG. 5 is a perspective view of the specially designed shaft of the current application.

FIG. 4 is a cross sectional view of the part marked as the line A-A in FIG. 2 seen from the bottom side of the toothbrush (1). And FIG. 5 is a perspective view of the specially designed scrubbing shaft (12) of the current application. The scrubbing shaft (12) positioned above the motor gear (5), which passes through the center of the first end plate (8). The scrubbing shaft (12) has an annular portion (13) at one end. This side of the scrubbing shaft (12) is retractably anchored to the first end plate (8). Grooves (12-G) are developed on both sides of the annular portion (13) on which bearing equipped ring connectors (10) are engaged. The other end of the scrubbing shaft is connected to a replaceable toothbrush head (14) as shown in the FIG. 2 via a holding shaft (15). Another groove (16-G) is developed to engage another bearing equipped ring connector (10) that rotatably holds the scrubbing shaft (12) on the brush head side. The replacable toothbrush head (14) is engaged to the holding shaft (15) with the aid of pressing protrusions (17) developed inwardly.

Figure 6A:
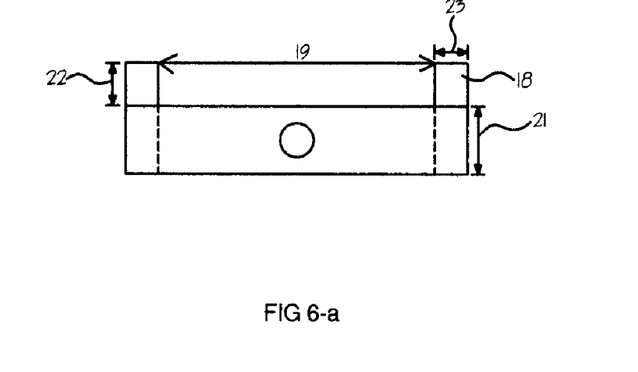
Figure 6B:
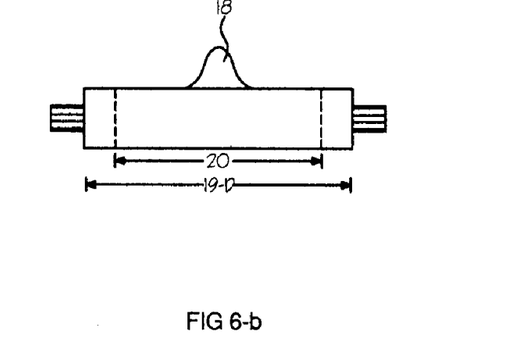
Figure 6C:
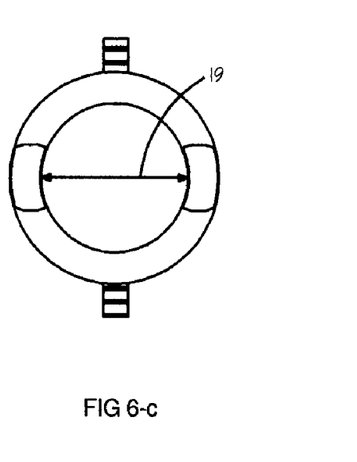

FIG. 6-*a* and FIG. 6-*b* are side views of the first embodiment of the annular portion 'B' of the specially designed shaft (12) of the current application seen from the bottom and side of the tooth brush (1), respectively. FIG. 6-*c* is an over view of the first embodiment of the portion 'B'. Two small protrusions (18) are developed on the brim of the annular portion, locating each other at the most farthest distance. The line (19) connecting these two protrusions (18) and the scrubbing shaft (12) forms a rectangular. The annular portion (13) has dimension of 10 to 15 mm in outer diameter (19-D) and 8 to 13 mm in inner diameter (20) and thickness (21) of 3 to 5 mm. The protrusions (18) have height (22) of 3 to 5 mm. The thickness (23) of the protrusions (18) is 2 mm.

Figure 7A:
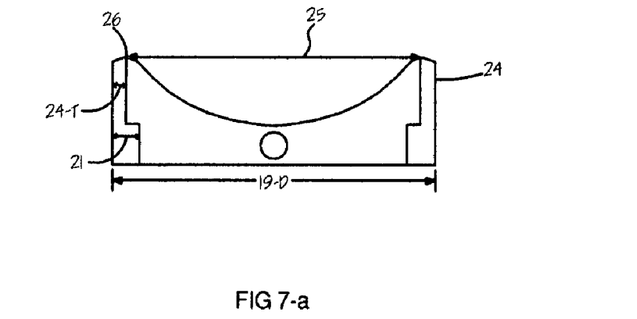
Figure 7B:
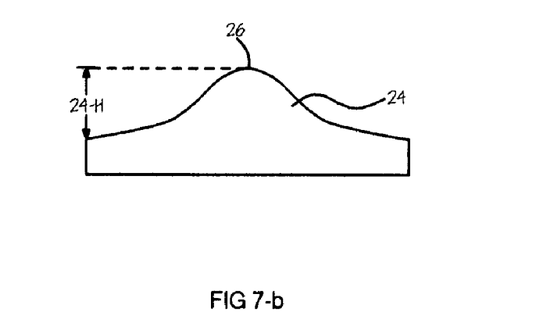
Figure 7C:
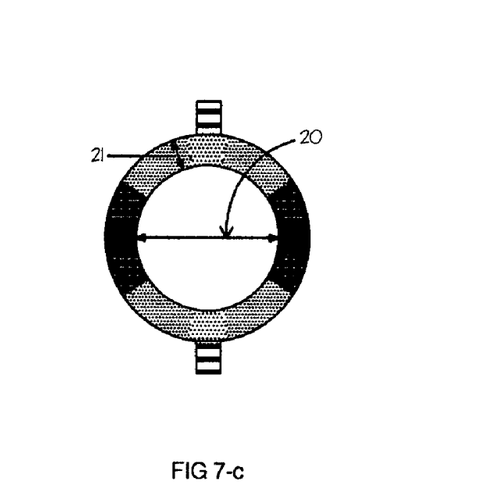

FIG. 7-*a* and FIG. 7-*b* are side views of the second embodiment of the annular portion 'B' of the specially designed shaft (12) of the current application seen from the bottom and side of the tooth brush (1), respectively. FIG. 7-*c* is an over view of the second embodiment of the portion 'B'. Two small arc wing shape protrusions (24) are developed on the brim of the annular portion. The bottom ends of the both wing shape protrusion (24) are connected each other. The line (25) connecting the highest points (26) of these two protrusions (24) and the scrubbing shaft (12) forms a rectangular. The annular portion 'B' has dimension of 10 to 15 mm in outer diameter (19) and 8 to 13 mm in inner diameter (20) and thickness (21) of 3 to 5 mm. The protrusions (24) have height (24-H) of 3 to 5 mm. The thickness (24-T) of the protrusions (24) is 2 mm.

Figure 8:
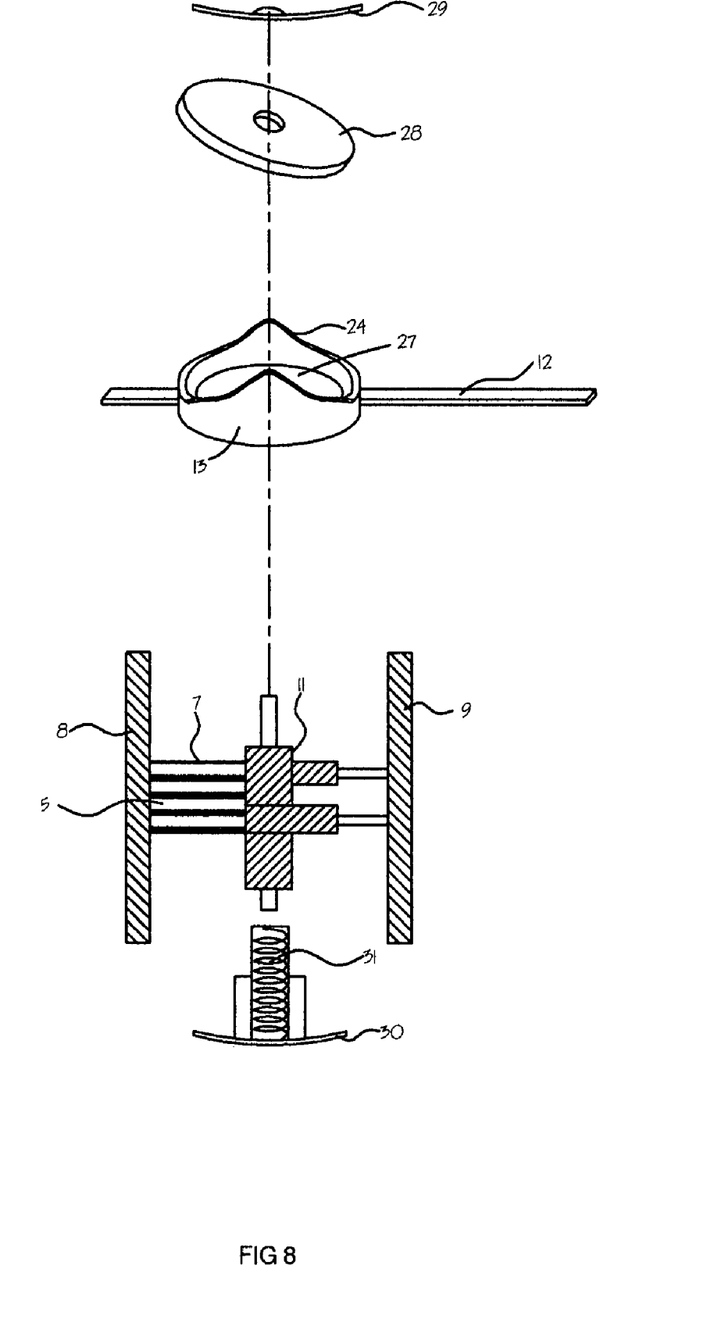
FIG. 8 is a perspective exploded view of the gears and shaft of the current application.

FIG. 8 is a perspective exploded view of the gears and the scrubbing shaft (12) of the current application. The perpendicularly coupled scrubbing gear (11) is located to penetrate the central hollow portion (27) of the annular portion (13) of the scrubbing shaft (12). A circular plate (28) is attached to the perpendicularly coupled scrubbing gear (11) with an angle by allowing the gear (11) penetrates the center of the circular plate (28). Both ends of the perpendicularly coupled gear (11) are rotatably anchored to the upper (29) and bottom (30) inner surface of the space formed between the first (8) and second (9) end plates. Two button type springs (31) are located below the annular portion (13) to push up the portion (13).

Figure 9:
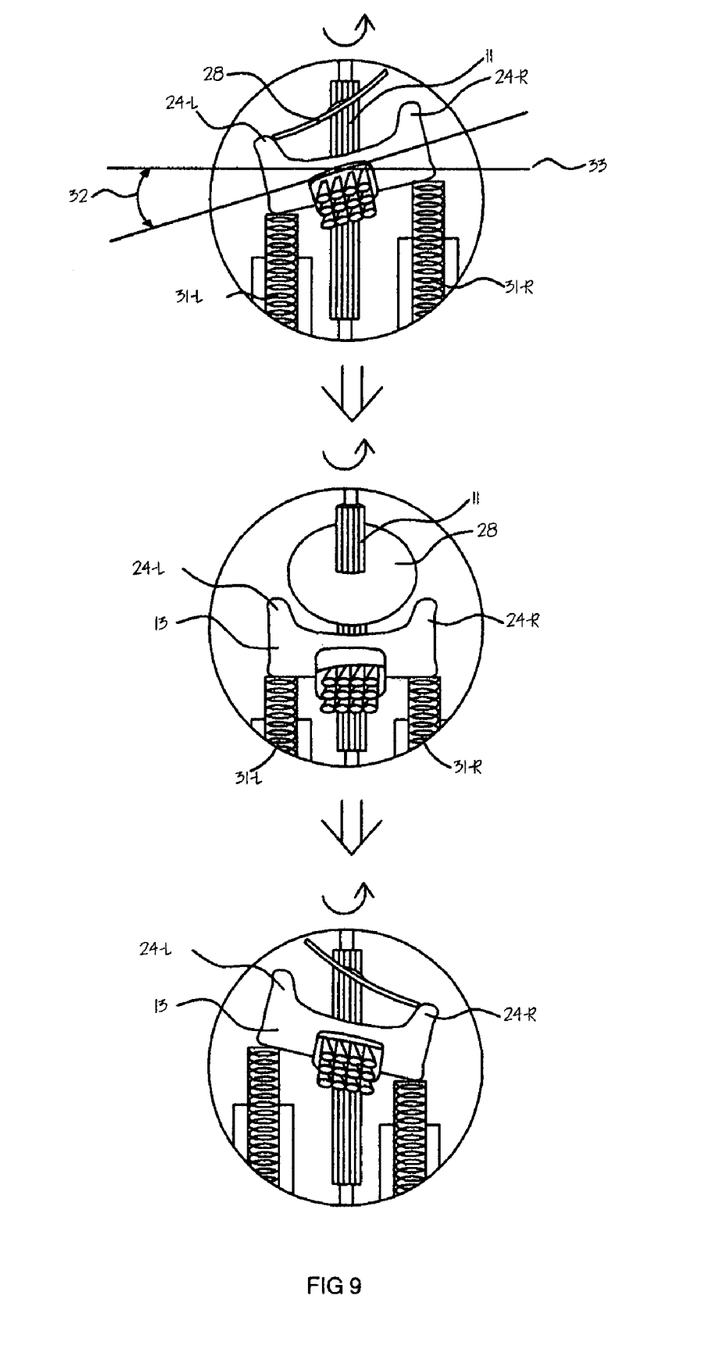
FIG. 9 is schematic drawings show how the brush head moves oscillatory according to motion of the circular plate, shaft and gears seen from the brush head side.

FIG. 9 is a schematic drawings show how the replacable tooth brush head (14) moves oscillatorily according to motion of the circular plate (28), shaft (12) and gears (7), (5) and (11) seen from the brush head side. The circular plate (28) is affixed to the perpendicularly coupled scrubbing gear (11) with a predetermined angle (32) of 10 to 30 degree from the horizontal line (33). When the circular plate (28) faces left side of the drawing, the plate (28) suppresses the wing shape protrusion of the left side seen from the FIG. 9, left wing (24-L). Then the left wing (24-L) and the left side of the annular portion (13) are lowered. As a result, the replacable toothbrush head (14) leans toward to the left. At this moment, the left side of the annular portion (13) presses the left spring (31-L). As the perpendicularly coupled scrubbing gear (11) turns, the circular plate (28) turns too. The left spring (31-L) pushes up the left side of the annular portion (13). When the circular plate (28) faces front, the annular portion (13) and the replaceable toothbrush head (14) take a horizontal position with an additional aid of the spring (31-L). Same situation happens when the circular plate (28) faces to the rear side, brush handle (4). As the scrubbing gear (11) turns further, the circular plate (28) presses the right wing (24-R) of the protrusion and the replaceable toothbrush head (14) leans toward to the right side. When the circular plate (28) faces rear side, the brush positions in horizontal.

By the mechanism described above, the replaceable toothbrush head (14) of the current application continues the oscillatory motion as far as the motor (2), motor gear (5), scrubbing gears ((7) and (11)) turns in one direction.

Applications of the assembly of the gears and parts, introduced above, to other utilities with minor changes are very easy for every personnel.

What is claimed is:

1. An electric motor driven tooth brush equipped with latitude oscillating scrubbing brush head is comprised of;
    a rechargeable battery accommodated in a cylindrical chamber of a housing of a handle portion of a toothbrush; and
    a motor gear attached to a rotating shaft of an electric motor and rotatably supported on a first end plate and a second end plate of the housing via a bearing equipped ring connector; and
    two scrubbing drive gears each having straight blades and sloped blades in one body and is coupled to the motor gear and rotatably supported on the first end plate and second end plate of the housing via bearing equipped ring connector; and
    another scrubbing gear with only sloped blades and is perpendicularly coupled to the two scrubbing drive gears; and
    a scrubbing shaft having an annular portion, which has two arc shape protrusions developed on an upper side thereof located opposite each other at a most farthest distance, at one end to allow the perpendicularly coupled scrubbing gear pass through thereof, and which is positioned above the motor gear by rotatably anchored at one end thereof to the first end plate and the other end thereof is connected to a replaceable tooth brush head via a holding shaft; and
    a replaceable toothbrush head that is engaged to the scrubbing shaft with the aid of pressing protrusions developed inwardly at the other end of the scrubbing shaft; and
    a circular plate that is attached to the perpendicularly coupled scrubbing gear with a predetermined angle by allowing the scrubbing gear to penetrate the center of the circular plate and both ends thereof are rotatably anchored to an upper and bottom inner surface of a space formed between the first and second end plates; and
    two springs located just below the protrusions on the annular portion to push up the annular portion.

2. An electric motor driven toothbrush equipped with latitude oscillating scrubbing brush head of claim 1, wherein the predetermined angle between the perpendicularly coupled scrubbing gear and the circular plate is 23 degree.

* * * * *